United States Patent [19]
Bhatnagar et al.

[11] Patent Number: 5,760,003
[45] Date of Patent: Jun. 2, 1998

[54] HEMOREGULATORY PEPTIDES

[75] Inventors: Pradip Kumar Bhatnagar, Exton; William Francis Huffman, Malvern, both of Pa.

[73] Assignee: SmithKline Beecham Corporation, Philadelphia, Pa.

[21] Appl. No.: 244,415

[22] PCT Filed: Nov. 24, 1992

[86] PCT No.: PCT/US92/10070

§ 371 Date: May 25, 1994

§ 102(e) Date: May 25, 1994

[87] PCT Pub. No.: WO93/10807

PCT Pub. Date: Jun. 10, 1993

Related U.S. Application Data

[63] Continuation-in-part of Ser. No. 799,465, Nov. 26, 1991, abandoned.

[51] Int. Cl.⁶ ............... A61K 38/00; C07K 7/00; C07K 7/06
[52] U.S. Cl. ............... 514/17; 530/329; 530/330
[58] Field of Search ............... 514/17; 530/330, 530/329

[56] References Cited

U.S. PATENT DOCUMENTS 4,499,081  2/1985  Laerum ............... 514/17

FOREIGN PATENT DOCUMENTS

WO 87/00180  1/1987  WIPO ............... C07K 7/06
WO 90/02753  3/1990  WIPO ............... C07K 7/06
WO 90/02754  3/1990  WIPO ............... C07K 7/06

OTHER PUBLICATIONS

Broxmeger, The American Journal of Pediatric Hematology/Oncology, 14(1) pp. 22–30, 1992.

Wlodawer et al, Science, 245, pp. 616–621, 1989.

Reichelt, et al. "Isolation and Structure of an Epidermal Mitosis Inhibiting Pentapeptide", Biochem, and Biophy, Res. Comm. 146: 1493–1501 (1987).

Wlodawer, et al., "Conserved Folding Retroviral Proteases: Crystal Structure of a Synthetic HIV-1 Protease", Science 245: 616–621 (1989).

Paukovits, et al., "Hemoregulatory Peptide pGlu–Glu–Asp–Cys–Lys: A New Synthetic Derivative for Avoiding Dimerization and Loss of Inhibioty Activity", Mol. Pharm. 38: 401–409 (1990).

Paukovits, et al., "Protection from Arabinofuranosylcytosine and n-Mustard-Induced Myelotoxicity Using Hemoregulatory Peptide pGlu–Glu–Asp–Cys–Lys Monomer and Dimer", Blood 77: 1313–1319 (1991).

Primary Examiner—Cecilia J. Tsang
Assistant Examiner—S. G. Marshall
Attorney, Agent, or Firm—Linda E. Hall; Stephen A. Venetianer; Edward T. Lentz

[57] ABSTRACT

The present invention relates to novel peptides which have hemoregulatory activities and can be used to inhibit the myelopoietic system of humans and animals.

7 Claims, No Drawings

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
        ( A ) NAME/KEY: Peptide
        ( B ) LOCATION: 1 and 4
        ( D ) OTHER INFORMATION: /note= "First Xaa = pyroglutanic acid, second is aminobutyric acid"

( x i ) SEQUENCE DESCRIPTION: SEQ ID NO:1:

Xaa Glu Asp Xaa Lys
    1                   5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
        ( A ) NAME/KEY: Peptide
        ( B ) LOCATION: 1 and 4
        ( D ) OTHER INFORMATION: /note= "First Xaa is picolinic acid, second is aminobutyric acid"

( x i ) SEQUENCE DESCRIPTION: SEQ ID NO:2:

Xaa Glu Asp Xaa Lys
    1                   5

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
        ( A ) NAME/KEY: Peptide
        ( B ) LOCATION: 1 and 4
        ( D ) OTHER INFORMATION: /note= "First Xaa is picolinic acid, second is aminobutyric acid"

( x i ) SEQUENCE DESCRIPTION: SEQ ID NO:3:

Xaa Ser Asp Xaa Lys
    1                   5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: Not Relevant -continued (D) TOPOLOGY: linear (ii) MOLECULE TYPE: peptide (ix) FEATURE:
 (A) NAME/KEY: Peptide
 (B) LOCATION: 1 and 4
 (D) OTHER INFORMATION: /note= "First Xaa is pyroglutamic
  acid, second is aminobutyric acid"

(xi) SEQUENCE DESCRIPTION: SEQ ID NO:4:

Xaa Glu Asp Xaa Tyr Lys
1      5

(2) INFORMATION FOR SEQ ID NO:5:

(i) SEQUENCE CHARACTERISTICS:
 (A) LENGTH: 5 amino acids
 (B) TYPE: amino acid
 (C) STRANDEDNESS: Not Relevant
 (D) TOPOLOGY: linear (ii) MOLECULE TYPE: peptide (ix) FEATURE:
 (A) NAME/KEY: Peptide
 (B) LOCATION: 1 and 5
 (D) OTHER INFORMATION: /note= "First Xaa is pyroglutamic
  acid, second is Gly-OH"

(xi) SEQUENCE DESCRIPTION: SEQ ID NO:5:

Xaa Glu Asp Lys Xaa
1     5

(2) INFORMATION FOR SEQ ID NO:6:

(i) SEQUENCE CHARACTERISTICS:
 (A) LENGTH: 5 amino acids
 (B) TYPE: amino acid
 (C) STRANDEDNESS: Not Relevant
 (D) TOPOLOGY: linear (ii) MOLECULE TYPE: peptide (ix) FEATURE:
 (A) NAME/KEY: Peptide
 (B) LOCATION: 1
 (D) OTHER INFORMATION: /note= "Xaa is pyrolutanic acid"

(xi) SEQUENCE DESCRIPTION: SEQ ID NO:6:

Xaa Glu Asp Ser Gly
1     5

(2) INFORMATION FOR SEQ ID NO:7:

(i) SEQUENCE CHARACTERISTICS:
 (A) LENGTH: 5 amino acids
 (B) TYPE: amino acid
 (C) STRANDEDNESS: Not Relevant
 (D) TOPOLOGY: linear (ii) MOLECULE TYPE: peptide (ix) FEATURE:
 (A) NAME/KEY: Peptide
 (B) LOCATION: 1 and 5
 (D) OTHER INFORMATION: /note= "First Xaa is picolinic
  acid, second is Lys-OH"

(xi) SEQUENCE DESCRIPTION: SEQ ID NO:7:

Xaa Glu Asp Ser Xaa
1     5

( 2 ) INFORMATION FOR SEQ ID NO:8:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: linear ( i i ) MOLECULE TYPE: peptide ( i x ) FEATURE:
    ( A ) NAME/KEY: Peptide
    ( B ) LOCATION: 1, 4 and 5
    ( D ) OTHER INFORMATION: /note= "First Xaa is picolinic
           acid, second is aminobutyric acid, third is Lys-OH"

( x i ) SEQUENCE DESCRIPTION: SEQ ID NO:8:

```
Xaa  Ser  Asp  Xaa  Xaa
1                    5
```

( 2 ) INFORMATION FOR SEQ ID NO:9:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: linear ( i i ) MOLECULE TYPE: peptide ( i x ) FEATURE:
    ( A ) NAME/KEY: Peptide
    ( B ) LOCATION: 1, 4 and 5
    ( D ) OTHER INFORMATION: /note= "First Xaa is pyroglutamic
           acid, second is aminobutyric acid, third is Lys-OH"

( x i ) SEQUENCE DESCRIPTION: SEQ ID NO:9:

```
Xaa  Glu  Asp  Xaa  Xaa
1                    5
```

( 2 ) INFORMATION FOR SEQ ID NO:10:

( i ) SEQUENCE CHARACTERISTICS:
    ( A ) LENGTH: 6 amino acids
    ( B ) TYPE: amino acid
    ( C ) STRANDEDNESS: Not Relevant
    ( D ) TOPOLOGY: linear ( i i ) MOLECULE TYPE: peptide ( i x ) FEATURE:
    ( A ) NAME/KEY: Peptide
    ( B ) LOCATION: 1, 4 and 6
    ( D ) OTHER INFORMATION: /note= "First Xaa is pyrogultamic
           acid, second is aminobutyric acid, third is Lys-OH"

( x i ) SEQUENCE DESCRIPTION: SEQ ID NO:10:

```
Xaa  Glu  Asp  Xaa  Tyr  Xaa
1                    5
```

( 2 ) INFORMATION FOR SEQ ID NO:11:

( i ) SEQUENCE CHARACTERISTICS:
    ( A ) LENGTH: 6 amino acids
    ( B ) TYPE: amino acid
    ( C ) STRANDEDNESS: Not Relevant
    ( D ) TOPOLOGY: linear ( i i ) MOLECULE TYPE: peptide ( i x ) FEATURE:
    ( A ) NAME/KEY: Protein
    ( B ) LOCATION: 1, 4 and 6

-continued (D) OTHER INFORMATION: /note= "First Xaa is pyroglutamic acid, second is aminobutyric acid, third is Tyr-OH"

(xi) SEQUENCE DESCRIPTION: SEQ ID NO:11:

```
Xaa Glu Asp Xaa Lys Xaa
 1               5
```

HEMOREGULATORY PEPTIDES

This application is a 371 of PCT/US 92/10070 filed Nov. 24, 1992. This application is also a continuation-in-part of Ser. No. 07/799466 filed Nov. 26, 1991, now abandoned.

FIELD OF THE INVENTION

The present invention relates to novel peptides which have hemoregulatory activities and can be used to inhibit the myelopoietic system of humans and animals.

BACKGROUND OF THE INVENTION

A variety of regulatory messengers and modifiers such as colony stimulating factors, interferons, and different types of peptides are responsible for the regulation of myelopoiesis. Metcalf, *Cell*, 43:5 (1985); Baserga R., Foa P., Metcalf D., Polli EE (eds), *Biological Regulation of Cell Proliferation* (1986); Nicola et al., *J. Cell Physiol.* 128:501 (1986), Zoumbos et al., *Proyr. Hemat.* 1:341 and 14:201 (1986); Werner et al., *Experientia* 42:521 (1986). Over twenty years ago, Rytomaa and Kivieniemi *Cell Tissue Kinet* 1:329–340 (1968); Rytomaa et al., *Control of Cellular Growth in Adult Organisms* pp 106–138 (1967) reported that extracts of mature granulocytes (granulocytic chalone) could specifically inhibit rat myelopoietic cell proliferation in cover slip cultures. Later, they demonstrated that the factor, which had a molecular weight less than 3,000 daltons, was able to induce the regression of a transplantable rat granulocytic leukemia, as well as retard the growth of leukemia cells in humans. Paukovits and others extracted a similar factor from rat bone marrow cells and showed that it inhibited the titrated thymidine uptake of bone marrow cells, Paukovits, W. R., *Cell Tissue Kinet* 4:539–547 (1971); Naturforsch 37:1297 (1982). In 1979, Boll et al., *Acta Haematologica* 6:130 (1979) demonstrated the inhibitory effects of rat granulocytic extracts on human bone marrow cells in culture and a number of other researchers demonstrated that this crude granulocytic extract inhibited the development of g-CFUC and/or gm-CFUC in vitro from rodent bone marrow cells.

This biological agent was termed a granulocyte chalone which, according to this theoretical concept, should be an endogenous inhibitor of cell proliferation acting in the same tissue as it was secreted. The material obtained from crude extracts was found to be non-species specific but highly tissue specific. Furthermore, it was found to be nontoxic and to have reversible activities.

In 1982, a synthetic hemoregulatory pentapeptide was reported to have a selective inhibitory effect on myelopoietic cells both in vitro and in vivo, where the main effect seems to be on myelopoietic stem cells (CFU-gm), Paukovits et al., Z. Naturforsch 37:1297 (1982) and U.S. Pat. No. 4,499,081. This peptide is believed to be an analogue of a naturally occurring granulopoiesis inhibition factor which has been found in minute quantities in bone marrow extracts.

We have now found certain synthetic peptides which have a selective inhibitory effect on myelopoietic cells in vitro. These peptides, by inhibiting haematopoiesis, and, in particular, granulopoiesis tend to prevent quiescent cells from entering into cell division and so becoming susceptible to attack by cytotoxic anti-cancer drugs. In addition to providing a protective function in therapy using cytotoxic drugs, the peptides may also be used to arrest proliferation of cancer cells related to the myelopoietic system, i.e. myeloid leukemia.

SUMMARY OF THE INVENTION

This invention comprises peptides, hereinafter represented as formula (I), which have hemoregulatory activities and can be used to inhibit haematopoiesis.

The peptides are useful in providing a protective function in therapy using irradiation and/or cytotoxic drugs, and may also be used to arrest proliferation of cancer cells related to the myelopoietic system, for example, in the treatment of myeloid leukemia. The peptides may also be used in many clinical situations where it is desirable to alter hemopoiesis.

These compounds may also be used in combination with the dimers of co-pending U.S. application Ser. No. 071,547, 730, incorporated by reference herein, to provide alternating peaks of high and low activity in the bone marrow cells, thus augmenting the natural circadian rhythm of haematopoiesis. In this way, cytostatic therapy can be given at periods of low bone marrow activity, thus reducing the risk of bone marrow damage, while regeneration will be promoted by the succeeding peak of activity. This invention is also a pharmaceutical composition, which comprises a compound of formula (I) and a pharmaceutically acceptable carrier.

This invention further constitutes a method for inhibiting the myelopoietic system of an animal, including humans, which comprises administering to an animal in need thereof, an effective amount of a compound of formula (I).

DETAILED DESCRIPTION OF THE INVENTION

The peptides of this invention are illustrated by the formula (I):

$$A\text{-}B\text{-}C\text{-}D\text{-}(X)_n\text{-}E \qquad (I)$$

wherein:

A is picolinic acid, pyroglutamic acid, proline or L-pipecolinic acid,

B is serine, glutamic acid, aspartic acid, threonine, cysteine or tyrosine;

C is aspartic acid or glutamic acid;

D is aminobutyric acid, alanine, propargyl glycine, glycine, serine, cysteine or β alanine;

X is tyrosine or lysine;

n is 0 or 1;

E is —N($R_1$)—$R_2R_3$ or E is glycine, lysine, ornithine, tyrosine, para-aminophenylalanine or the carboxamide or hydroxymethyl derivative thereof;

$R_1$, $R_4$ and $R_5$ are independently hydrogen, $C_{1-5}$ alkyl, phenyl, napthyl or $C_{5-7}$ cycloalkyl;

$R_2$ is $C_{1-6}$ alkyl, phenyl, naphthyl or $C_{5-7}$ cycloalkyl;

$R_3$ is —$NR_4R_5$ or aziridinyl, pyrrolidinyl, imidazolyl, pyrrolyl, piperidinyl, piperazinyl, morphollinyl, pyrrolidinyl or pyrralinyl; provided the compound of formula (I) is not p-Glu-Glu-Asp-Cys-Lys; or a pharmaceutically acceptable salt thereof.

Also included in this invention are pharmaceutically acceptable salt complexes of the compounds of this invention. It should be noted in formula (I) E comprises the terminal carboxyl group of the amino acid residue corresponding to glycine, lysine, ornithine para-aminophenylalanine or the carboxamide or hydroxy methyl derivatives thereof or E is the amide group of the —N($R_1$) —$R_2R_3$ group.

The abbreviations and symbols commonly used in the art are used herein to describe the peptides:

ala=alanine
pGlu=pyroglutamic acid
Pro=proline
Glu=glutamic acid

Asp=aspartic acid
Tyr=tyrosine
Pic=picolinic acid
Ppc=L-pipecolinic acid
Abu=aminobutyric acid
Ppg=propargyl glycine
Gly=glycine
Orn=ornithine
p-(NH$_2$)Phe=para-aminophenylalanine
Hna=2,6-diamino-4-hexynoic acid
Lys=lysine
Cad=cadaverine In accordance with conventional representation, the amino terminus is on the left and the carboxy terminus is on the right. All chiral amino acids may be in the D or L absolute configuration.

The amino terminus may be protected by acylation. Examples of such protecting groups are, t-butoxycarbonyl (t-Boc), CH$_3$CO and Ar—CO (Ar=benzyl, or phenyl).

The C-terminus may be carboxy as in the case of the natural amino acid or the carboxamide

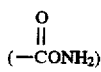
(—CONH$_2$)

or hydroxymethyl (—CH$_2$—OH).

Preferred compounds are those in which:

A is pyroglutamic acid or picolinic acid;

B is glutamic acid or serine;

C is aspartic acid;

D is aminobutyric acid;

E is glycine or lysine; and n is 0;

and the chiral amino acids are in the L absolute configuration.

Especially preferred is pGlu-Glu-Asp-Abu-Lys (SEQ ID NO: 1) and Pic-Ser-Asp-Abu-Lys (SEQ ID NO: 3). The peptides of the invention are prepared by the solid phase technique of Merrifield, *J. Am. Chem. Soc.*, 85, 2149 (1964), or solution methods known to the art may be successfully employed. The methods of peptide synthesis generally set forth in J. M. Stewart and J. D. Young, "*Solid Phase Peptide Synthesis*", Pierce Chemical Company, Rockford, Ill. (1984) or M. Bodansky, Y. A. Klauser and M. A. Ondetti, "*Peptide Synthesis*", John Wiley & Sons, Inc., New York, N.Y. (1976) may be used to produce the peptides of this invention and are incorporated herein by reference.

Each amino acid or peptide is suitably protected as known in the peptide art. For example, the a-fluoroenylmethyloxycarbonyl group (Fmoc) or t-butoxycarbonyl (t-Boc) group are preferred for protection of the amino group, especially at the α-position. A suitably substituted carbobenzoxy group may be used for the ε-amino group of lysine and benzyl group for the β and γ carboxy groups of Asp and Glu respectively. Suitable substitution of the carbobenzoxy protecting group is ortho and/or para substitution with chloro, bromo, nitro or methyl, and is used to modify the reactivity of the protective group. Except for the t-Boc group, the protective groups are, most conveniently, those which are not removed by mild acid treatment. These protective groups are removed by such methods as catalytic hydrogenation, sodium in liquid ammonia or HF treatment as known in the art.

If solid phase synthetic methods are used, the peptide is built up sequentially starting from the carboxy terminus and working toward the amino terminus of the peptide. Solid phase synthesis is begun by covalently attaching the C terminus of a protected amino acid to a suitable resin, such as benzhydrylamine resin (BHA), methylbenzhydrylamine resin (MBHA) or chloromethyl resin (CMR), as is generally set forth in U.S. Pat. No. 4,244,946 or phenyl acid amino methyl resin (PAM). A BHA or MBHA support resin is used if the carboxy terminus of the product peptide is to be a carboxamide. ACMR or PAM resin is generally used if the carboxy terminus of the product peptide is to be a carboxy group, although this may also be used to produce a carboxamide or ester.

The protective group on the a-amino group is removed by mild acid treatment (i.e. trifluoroacetic acid). Suitable deprotection, neutralization and coupling cycles known in the art are used to sequentially add amino acids without isolation of the intermediate, until the desired peptide has been formed. The completed peptide may then be deblocked and/or split from the carrying resin in any order.

Treatment of a resin supported peptide with HF or HBr/ acetic acid splits the peptide from the resin and produces the carboxy terminal amino acid as a carboxylic acid or carboxamide.

If an ester is desired, the CMR or Pam resin may be treated with an appropriate alcohol, such as methyl, ethyl, propyl, butyl or benzyl alcohol, in the presence of triethylamine to cleave the peptide from the resin and product the ester directly.

Esters of the peptides of this invention may also be prepared by conventional methods from the carboxylic acid precursor. Typically, the carboxylic acid is treated with an alcohol in the presence of an acid catalyst. Alternatively, the carboxylic acid may be converted to an activated acyl intermediate, such as an acid halide, and treated with an alcohol, preferably in the presence of a base.

The preferred method for cleaving a peptide from the support resin is to treat the resin supported peptide with anhydrous HF in the presence of a suitable cation scavenger, such as anisole or dimethoxybenzene. This method simultaneously removes all protecting groups, except a thioalkyl group protecting sulfur, and splits the peptide from the resin. Peptides hydrolyzed in this way from the CMR and Pam resins are carboxylic acids, those split from the BHA resin are obtained as carboxamides.

Modification of the terminal amino group of the peptide is accomplished by alkylation or acylation by methods generally known in the art. These modifications may be carried out upon the amino acid prior to incorporation into the peptide, or upon the peptide after it has been synthesized and the terminal amino group liberated, but before the protecting groups have been removed.

Typically, acylation is carried out upon the free amino group using the acyl halide, anhydride or activated ester, of the corresponding alkyl or aryl acid, in the presence of a tertiary amine. Mono-alkylation is carried out most conveniently by reductive alkylation of the amino group with an appropriate aliphatic aldehyde or ketone in the presence of a mild reducing agent, such a lithium or sodium cyanoborohydride. Dialkylation may be carried out by treating the amino group with an excess of an alkyl halide in the presence of a base.

Solution synthesis of peptides is accomplished using conventional methods used to for amide bonds. Typically, a protected t-Boc amino acid which has a free carboxyl group is coupled to a protected amino acid which has a free amino group using a suitable coupling agent, such as N,N'- dicyclohexyl carbodiimide (DCC), optionally in the presence of catalysts such as 1-hydroxybenzotriazole (HOBT) or dimethylamino pyridine (DMAP). Other methods, such as the formation of activated esters, anhydrides or acid halides, of the free carboxyl of a protected t-Boc-amino-acid, and subsequent reaction with the free amine of a protected amino acid, optionally in the presence of a base, are also suitable. For example, a protected Boc-amino acid or peptide is treated in an anhydrous solvent, such as methylene chloride or tetrahydrofuran (THF), in the presence of a base, such as N-methyl morpholine, DMAP (dimethylaminopyridine) or a trialkyl amine, with isobutyl chloroformate to form the "activated anhydride", which is subsequently reacted with the free amine of another protected amino acid or peptide. The peptide formed by these methods may be deprotected selectively, using conventional techniques, at the amino or carboxy terminus and coupled to other peptides or amino acids using similar techniques. After the peptide has been completed, the protecting groups may be removed as hereinbefore described, such as by hydrogenation in the presence of a palladium or platinum catalyst, treatment with sodium in liquid ammonia, hydrofluoric acid or alkali.

If the final peptide, after it has been deprotected, contains a basic group, an acid addition salt may be prepared. Acid addition salts of the peptides are prepared in a standard manner in a suitable solvent from the parent compound and a slight excess of an acid, such a hydrochloric, hydrobromic, sulfuric, phosphoric, acetic, maleic, succinic or methane-sulfonic. The acetate salt for is especially useful. If the final peptide contains an acidic group, cationic salts may be prepared. Typically the parent compound is treated with a slight excess of an alkaline reagent, such as a hydroxide, carbonate or alkoxide, containing the appropriate cation. Cations such as $Na^+$, $K^+$, $Ca^{++}$ and $NH_4^+$ are examples of cations present in pharmaceutically acceptable salts. $Na^+$ and $NH_4^+$ are especially preferred.

In general, in order to exert a inhibitory effect, the peptides of the invention may be administered to human patients by injection in the dose range of about 0.5 ng to about 10 mg, for example about 5–500 ng, or orally in the dose range of about 50 ng to about 5 mg, for example about 0.1 ng to 1 mg per 70 kg body weight per day; if administered by infusion or similar techniques, the dose may be in the range of about 0.005 ng to about 10 mg per 70 kg body weight, for example about 0.03 ng to 1 mg over six days. In principle, it is desirable to produce a concentration of the peptide of about $10^{-15}M$ to about $10^{-5}M$ in the extracellular fluid of the patient.

According to a still further feature of the present invention there are provided pharmaceutical compositions comprising as active ingredient one or more compound of formula (I) as hereinbefore defined or physiologically compatible salts thereof, in association with a pharmaceutical carrier or excipient. The compositions according to the invention may be presented for example, in a form suitable for oral, nasal, parenteral or rectal administration.

As used herein, the term "pharmaceutical" includes veterinary applications of the invention. These peptides may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline and water. Solid carriers include starch, lactose, calcium sulfate dihydrate, terra alba, magnesium stearate or stearic acid, talc, pectin, acacia, agar or gelatin. The carrier may also include a sustained release material such a glyceryl monostearate or glyceryl distearate, alone or with a wax. The amount of solid carrier varies but, preferably will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. Capsules containing one or several active ingredients may be produced, for example, by mixing the active ingredients with inert carriers, such as lactose or sorbitol, and filling the mixture into gelatin capsules. When a liquid carrier is used, the preparation will be in the form of a syrup, elixir, emulsion or an aqueous or non-aqueous suspension. Such a liquid formulation may be administered directly p.o. or filled into a soft gelatin capsule. Organ specific carrier systems may also be used.

Alternately pharmaceutical compositions of the peptides of this invention, or derivatives thereof, may be formulated as solutions of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration and contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

For rectal administration, a pulverized powder of the peptides of this invention may be combined with excipients such as cocoa butter, glycerin, gelatin or polyethylene glycols and molded into a suppository. The pulverized powders may also be compounded with an oily preparation, gel, cream or emulsion, buffered or unbuffered, and administered through a transdermal patch.

Nasal sprays may be formulated similarly in aqueous solution and packed into spray containers either with an aerosol propellant or provided with means for manual compression.

Dosage units containing the compounds of this invention preferably contain 1 mg–100 mg, for example 0.1–50 mg of the peptide of formula (I) or salt thereof.

According to a still further feature of the present invention there is provided a method of inhibition of myelopoiesis which comprises administering an effective amount of a pharmaceutical composition as hereinbefore defined to a subject.

No unacceptable toxicological effects are expected when compounds of the invention are administered in accordance with the present invention.

Biological Assays

A. In Vitro Hematopoietic Assay

The following in vitro assay system quantitates positive or negative effects of the compounds of this invention on the entrance of granulocyte-macrophage progenitor cells (CFU-GM) into cell cycle following pulse exposure in vitro. Under soft agar culture conditions in the presence of appropriate hematopoietic growth factors, colonies of granulocytes and macrophages can be quantitated and arise specifically from the proliferation of single CFU-GM. In order to proliferate, CFU-GM must enter S-phase of the cell cycle. Exposure of bone marrow cells to $^3$H-Thymidine prior to the soft agar culture eliminates those CFU-GM which are actively proliferating, ie, are in S-phase of the cell cycle. This effect is quantitated by a decrease in total CFU-GM colonies quantitated in the agar assay. In comparison to controls, the degree of decrease or increase in colony counts provides an index of stimulation or inhibition, respectively, of CFU-GM proliferation.

Procedure:

Femoral bone marrow cells are obtained and suspended at a concentration of 6–9×10$^6$ cells/ml in McCoy's 5A medium supplemented with 10% fetal bovine serum, antibiotics, essential and non-essential amino acids, MEM vitamins, serine, asparagine, glutamine, sodium pyruvate and sodium bicarbonate. Replicate cultures are pulsed for 2 hours with compounds of the invention over a concentration range of 1 pg to 1 mg per ml final concentration and incubated at 37° C. in an atmosphere of 7% $CO_2$ in humidified air. Following incubation, the cultures are washed three times with assay medium to remove peptides, and exposed to 560 uCi of $^3$H-Thymidine (Specific Activity=20 Ci/mMole) for 20 minutes. After exposure, 0.5 ml of cold Thymidine (1 mg/ml stock solution) is added to each tube to stop the reaction. Cultures are washed three times and plated in the CFU-GM agar assay at a concentration of 75,000 cells per culture in media as described above and containing 0.3% agar and 10% v/v medium conditioned by spleen cells exposed to pokeweed mitogen as a source of hematopoietic growth factors. The cultures are incubated at 37° C., 7% $CO_2$ in humidified air for 5–7 days and CFU-GM colonies enumerated microscopically. The percentage of CFU-GM in S-phase is calculated by dividing colony counts from $^3$H-Thymidine treated cultures by those of untreated control cultures. These values are compared to similarly derived numbers from peptide exposed and untreated cells.

B. Measurement of Superoxide Formation

Polymorphonuclear neutrophils (PMNs) are the first-line defense against many invading pathogens including C. albicans. The assessment of ex vivo candidacidal-activity of PMNs from treated animals is important in determining the mode of action of therapeutic compounds in the C. albicans animal model. Superoxide is the major initial product of oxygen reduction in the respiratory burst of activated PMNs and the various species of oxygen radicals generated during the respiratory burst are directly or indirectly cytotoxic to invading pathogens. Therefore, the measurement of superoxide formation and release during stimulation is important in the assessment of the oxidative metabolism and subsequent cidal efficiency of phagocytic cells.

Procedure:

The compound or control is administered to normal mice IP daily for 7 days. Peripheral blood from individual treated animals was collected and pooled. PB-PMNs were purified by standard separation methods; (Boyum, A. 1968. "Isolation of mononuclear cells and granulocytes from human peripheral blood" Scand. J. Clin. Lab Invest. 21: 77–89); and cell suspensions from the different groups were standardized to contain equivalent numbers of PMNs/ml. For candidacidal assays sufficient PB-PMNs were added to quadruplicate tubes containing C. albicans yeasts and 10% normal mouse serum in balanced salt solution to result in a final E:T ratio of 10:1. PB-PMNs were omitted from control tubes. The tubes were incubated at 37° C. for 1 hr. The phagocytes were lysed and aliquots were plated onto agar plates. The plates were incubated for 48 hrs at which time the number of colony forming units (CFU) were enumerated and the percent reduction in CFU for each sample determined.

Superoxide dismutase-inhibitable superoxide anion production was quantitated in a microtiter ferricytochrome c reduction assay (1.5×10$^5$ PB-PMN/well) in 0.5% gelatin/balanced salt solution during exposure to soluble and particulate stimuli (phorbol 12-myristate 13-acetate (PMA) and serum-opsonized C. albicans, respectively). The nmoles of ferricytochrome c reduced/well (quadruplicate wells/pooled group) was determined following a 1 hr incubation. Baseline superoxide activity was determined in the absence of any stimuli. PMA and Candida stimulated activity were corrected for spontaneous superoxide production prior to data calculation. Data for PB-PMNs from each treatment group are expressed as the percent of control superoxide where control activity is that observed for PB-PMNs from PBS/serum-treated mice.

The examples which follow serve to illustrate this invention. The Examples are intended to in no way limit the scope of this invention, but are provided to show how to make and use the compounds of this invention.

In the examples, all temperatures are in degrees Centigrade. Amino acid analysis were performed upon a Dionex Autoión 100. Analysis for peptide content is based upon Amino Acid Analysis. FAB mass spectra were performed upon a VG ZAB mass spectrometer using fast atom bombardment. The abbreviations used are as follows:

Abu=Aminobutyric acid

Ala=alanine

Asp=aspartic acid t-Boc=tert. butyloxy carbonyl

Cad=cadaverine

Cl-Z=p-chlorobenzyloxy carbonyl (Z=benzyloxy carbonyl)

DCC=dicyclohexyl carbodiimide

DCM=dichloromethane

DIEA=diisopropylethyl amine

EDC=(N-ethyl-N'-)3-dimethylaminopropyl) carbodimide

Glu=glutamic-acid p-Glu=pyroglutamic acid

Tyr=tyrosine

Hna=diaminohexynoic acid

HOBT=hydroxybenzotriazole

Lys=lysine

NMP=N-methyl-2-pyrrolidinone

Pic=picolenic acid

Pro=proline

Ppg=propargyl glycine

Gln=glutamine

Gly=glycine

Orn=ornithine

EXAMPLE 1

(pGlu-Glu-Asp-Abu-Lys): (SEQ ID NO. 1) Mol. Form $C_{24}H_{38}N_6O_{11}$ Mol. Wt. 585.6

800 mg of BOC-Lys (Cl-Z)-PAM resin (0.5 mM, substitution=0.63 mM/g) was charged in an ABI Model 430 A Peptide Synthesizer. The target peptide was synthesized according to manufacturer suggested standard protocols using 2 mM of each amino acid. (Applied Biosystems Model 430A Peptide Synthesizer Users Manual Version 1–30, February 1987, Part number 000066). After completion of the synthesis, the resin peptide was washed with DCM and dried (1.665 g). The peptide resin (1.2 g) was charged in a cleavage apparatus and cleaved using 10 ml HF and 1 ml anisole at −15° C. for two hrs. After removal of HF, the resin was extensively washed with ether and the peptide extracted in glacial acetic acid. Most of the acetic acid was removed on a rotovap and the residue was diluted with water and lyophilized. Two hundred twenty milligrams of crude peptide were obtained. The pure peptide (130 mg) was obtained after column chromatography on a C-18 "Bond Elute"® column using acetonitrile/water/trifluoroacetic acid (TFA) buffer. Amino acid analysis: Asp 1.0 (1), Glu 1.98 (2), Abu 1.12(1), Lys 1.06 (1) FAB/MS MH⁺ 587.5

EXAMPLE 2

(Pic-Glu-Asp-Abu-Lys) (SEQ ID NO: 2) Mol. Form $C_{25}H_{36}N_6O_{10}$ Mol. Wt 580.6:

800 mg of BOC-Lys (Cl-Z)-PAM resin (0.5 mM/substitution 0.63 mM/g) was charged in an ABI Model 430 A Peptide Synthesizer. The target peptide was synthesized according to manufacturer suggested standard protocols using 2 mm of each amino acid. After completion of the synthesis, the resin peptide was washed with DCM and dried (1.6 g). The peptide resin (884 mg) was charged in the HF cleavage apparatus and cleaved using 10 ml HF and 1 ml anisole at −15° C. for two hrs. After removal of HF, the resin was extensively washed with ether and the peptide was extracted in glacial acetic acid. Most of the acetic acid was removed on a rotavap and the residue was diluted with water and lyophilized. Two hundred and fifty-one milligrams of crude peptide were obtained. After purification on a C-18 "Bond Elute"® column using acetonitrile/water/TFA buffer, 141 mg of pure peptide (HPLC purity 97%) was obtained. Amino acid analysis: Asp 1.0 (1), Glu 1.03 (1), Abu 1.12 (1), Lys 1.17 (1). Pic is not identified by amino acid analysis. FAB/MS 581.1

EXAMPLE 3

(Pic-Ser-Asp-Abu-Lys) (SEQ ID NO: 3) Mol. Form. $C_{23}H_{34}N_6O_9$ Mol. Wt 538.56:

Eight hundred fifty mg BOC-Lys (Cl-Z)-PAM resin (0.56 mm of resin) was charged in an ABI Model 430 A Peptide Synthesizer. The target peptide was synthesized according to manufacturer suggested standard protocols using 2 mm of each amino acid. After completion of the synthesis, the resin peptide was washed with DCM and dried (1.038 g). The peptide resin (1.03 g) was charged in the HF cleavage apparatus and cleaved using 10 ml HF and 1 ml anisole at −15° C. for two hrs. After removal of HF, the resin was extensively washed with ether and the peptide was extracted in trifluoroacetic acid. Most of the trifluoroacetic acid was removed on a rotavap and the residue was diluted with water and lyophilized. Two hundred and ninety-eight milligrams of crude peptide was obtained. After purification on a C-18 "Bond Elute"® column using acetonitrile/water/TFA buffer, 178 mg of pure peptide (HPLC purity 97%) was obtained. Amino acid analysis: Asp 1.0 (1), Ser 0.88 (1), Abu 1.12 (1), Lys 1.17 (1). Pic is not identified by amino acid analysis.

EXAMPLE 4

(pGlu-Glu-Asp-Abu-Tyr-Lys): (SEQ ID NO: 4) Mol. Form. $C_{33}H_{47}N_7O_{13}$ Mol. Wt 749.77

Eight hundred fifty mg BOC-Lys (Cl-Z)-PAM resin (0.56 mm of resin) was charged in ABI Model 430 A Peptide Synthesizer. The target peptide was synthesized according to the manufacturer's suggested standard protocols using 2 mm of each amino acid. After completion of the synthesis, the resin peptide was washed with DCM and dried (1.353 g). The peptide resin (1.3 g) was charged in the HF cleavage apparatus and cleaved using 10 ml HF and 1 ml anisole at −15° C. for two hrs. After removal of HF, the resin was extensively washed with ether and the peptide was extracted in trifluoroacetic-acid. Most of the trifluoroacetic acid was removed on a rotavap and the residue was diluted with water and lyophilized. Four hundred and fifty-four milligrams of crude peptide were obtained. The crude peptide (204.7 mg) was purified on a C-18 "Bond Elute"® column using acetonitrile/water/TFA buffer. 95.2 mg of peptide (HPLC purity 90%) was obtained. Amino acid analysis: pGlu+Glu 2.02 (2), Asp 1.0 (1), Tyr 0.94 (1), Lys 1.03 (1)

EXAMPLES 5–11

By the methods given above the following peptides were made.

Example 5 p-Glu-Glu-Asp-Cys-Gly-OH (SEQ ID NO: 5)
6 pGlu-Glu-Asp-Ser-Gly (SEQ ID NO: 6)
7 Pic-Glu-Asp-Abu-Lys-OH (SEQ ID NO: 7)
8 Pic-Ser-Asp-Abu-Lys-OH (SEQ ID NO: 8)
9 pGlu-Glu-Asp-Abu-Lys-OH (SEQ ID NO: 9)
10 pGlu-Glu-Asp-Abu-Tyr-Lys-OH (SEQ ID NO: 10)
11 pGlu-Glu-Asp-Abu-Lys-Tyr-OH (SEQ ID NO: 11)

EXAMPLE 12

Formulations for pharmaceutical use incorporating compounds of the present invention can be prepared in various forms and with numerous excipients. Examples of such formulations are given below.

Tablets/Ingredients

Per Tablet

| 1. | Active ingredient (Cpd of Form. I) | 40 mg |
|----|-----|-----|
| 2. | Corn Starch | 20 mg |
| 3. | Alginic acid | 20 mg |
| 4. | Sodium alginate | 20 mg |
| 5. | Mg stearate | 1.3 mg |
|    |     | 2.3 mg |

Procedure for tablets:

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its converion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then sterilized by filtration through a 0.22 micron membrane filter and sealed in sterile containers.

We claim:

1. A compound of formula I:

$$A-B-C-D-(X)_n-E \quad (I)$$

wherein

A is picolinic acid, pyroglutamic acid, proline or L-pipecolinic acid;

B is serine, glutamic acid, aspartic acid, threonine, cysteine or tyrosine;

C is aspartic acid or glutamic acid;

D is aminobutyric acid, alanine, glycine, or serine;

X is tyrosine or lysine;

n is 0 or 1;

E is —N($R_1$)—$R_2R_3$ or E is lysine, ornithine, tyrosine, para-aminophenylalanine or the carboxamide or hydroxymethyl derivative thereof;

$R_1$, $R_4$ and $R_5$ are independently hydrogen, $C_{1-5}$alkyl, phenyl, napthyl or $C_{5-7}$ cycloalkyl;

$R_2$ is $C_{1-6}$alkyl, phenyl, napthyl or $C_{5-7}$ cycloalkyl;

$R_3$ is —$NR_4R_5$ or a pharmaceutically acceptable salt thereof.

2. A compound of claim 1 wherein A is pyroglutamic acid or picolinic acid; B is glutamic acid or serine; C is aspartic acid; D is aminobutyric acid; E is glycine or lysine and n is 0.

3. A compound of claim 1 wherein the chiral amino acids are in the L absolute configuration.

4. A compound of claim 1 wherein n is 1 and E is glycine or lysine.

5. A compound of claim 1 selected from the group consisting of:

Pic-Glu-Asp-Abu-Lys (SEQ ID NO: 2)

pGlu-Glu-Asp-Abu-Tyr-Lys (SEQ ID NO: 4)

pGlu-Glu-Asp-Abu-Lys (SEQ ID NO: 1)

Pic-Ser-Asp-Abu-Lys (SEQ ID NO: 3).

6. A pharmaceutical composition comprising a compound of claim 1 and a pharmaceutical acceptable carrier.

7. A method of inhibiting the myelopoietic system which comprises administering to a subject in need thereof, an effective amount of a compound of claim 1.

* * * * *